(12) United States Patent
Wilstrup

(10) Patent No.: US 11,537,686 B2
(45) Date of Patent: Dec. 27, 2022

(54) METHOD OF DERIVING A CORRELATION

(71) Applicant: Abzu ApS, Nordhavn (DK)

(72) Inventor: Casper Wilstrup, Birkeroed (DK)

(73) Assignee: Abzu ApS, Nordhavn (DK)

( * ) Notice: Subject to any disclaimer, the term of this patent is extended or adjusted under 35 U.S.C. 154(b) by 0 days.

(21) Appl. No.: 17/096,258

(22) Filed: Nov. 12, 2020

(65) Prior Publication Data

US 2022/0147593 A1    May 12, 2022

(51) Int. Cl.
*G06F 17/15* (2006.01)
(52) U.S. Cl.
CPC .................................. *G06F 17/15* (2013.01)
(58) Field of Classification Search
CPC .......... G06F 17/10; G06F 17/11; G06F 17/15; G06F 17/153; G06F 17/18; G06N 20/20; G06N 5/00–006
See application file for complete search history.

(56) References Cited

U.S. PATENT DOCUMENTS

2008/0307399 A1* 12/2008 Zhou ...................... G06N 3/126
717/141

OTHER PUBLICATIONS

M. Schmidt et al., Distilling Free-Form Natural Laws from Experimental Data, Science, vol. 324, 2009 (Year: 2009).*
S.M. Udrescu et al., AI Feynman: A physics-inspired method for symbolic regression, Science Advances, Apr. 15, 2020 (Year: 2020).*
W. Cai et al., Heat transfer correlations by symbolic regression, International Journal of Heat and Mass Transfer, 49, 4352-4359, 2006 (Year: 2006).*
M. Cranmer et al., Discovering Symbolic Models from Deep Learning with Inductive Biases, arXiv:2006.11287v1 [cs.LG], Jun. 19, 2020 (Year: 2020).*
K.R. Brolos et al., An Approach to Symbolic Regression Using Feyn, arXiv:2104.05417v1 [cs.LG], 2021 (Year: 2021).*

* cited by examiner

*Primary Examiner* — Emily E Larocque
(74) *Attorney, Agent, or Firm* — Harness, Dickey & Pierce, P.L.C.

(57) ABSTRACT

A method of deriving a correlation between observed values from e.g. a process, where initial values are derived from ingredients or process parameters and a second value from a resulting product. A number of candidate mathematical functions are generated in a grid-type flow structure in which tokens flow through nodes, each node determining a mathematical function, so that a token defines a number of mathematical functions and an order thereof. Tokens may be combined so that the functions include multiple variables. A best, resulting mathematical function may be determined and the grid structure amended to favour this function and the method may be repeated.

Figure 1:
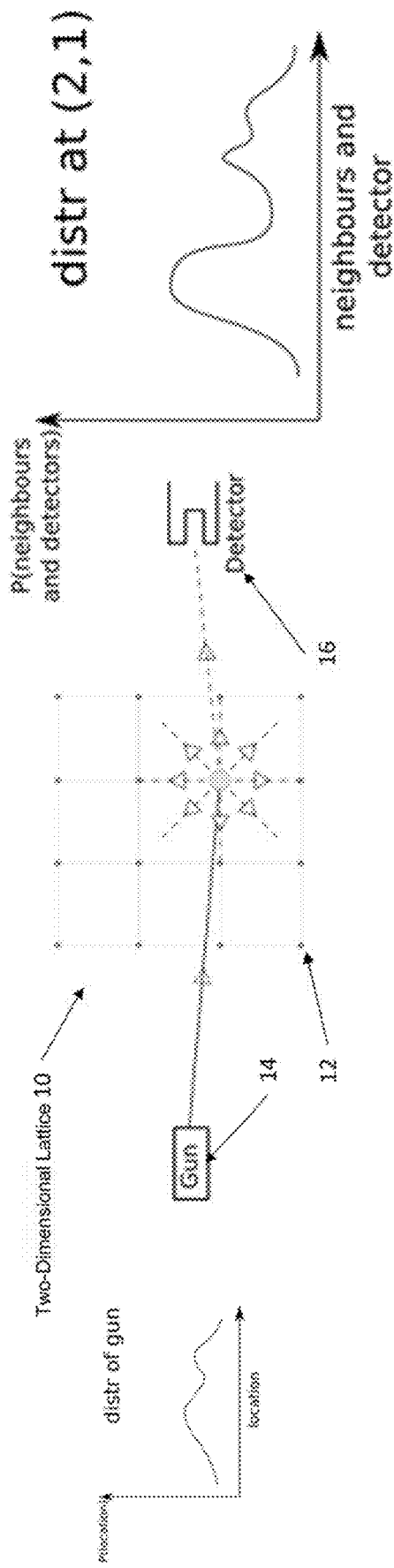

4 Claims, 3 Drawing Sheets

US 11,537,686 B2

METHOD OF DERIVING A CORRELATION

The present invention relates to a method of deriving a correlation and in particular a manner of deriving a correlation between input values and an output value, such as input values from parameters of a function, such as a production process, and an output value, such as from a product of the production process. The input values could be concentrations of ingredients, pH, temperature, or the like, and the output value could be a quality of the resulting product. The product could be brought about using enzymes, where the product quality could vary due to e.g. amino acid mutations of the enzymes. Thus, the input values could represent amino acid parameters (such as mutation or not and of which enzyme) and the output could relate to a quality or parameter of the resulting product.

Another example would be the determination of a correlation between a number of features of persons and an occurrence of a particular disease where the diagnosis of the disease is the output parameter.

A further example would be a process or condition in the human body, where the initial parameters may be physical parameters determined from the body, such as temperature, age, sex, concentration of a substance, a presence of a predetermined genetic defect or deviation, or the like, and where the second value or parameter may be a presence or not of a physical condition, such as a predetermined type of cancer or other condition. The second value or parameter may alternatively or additionally quantify the physical condition, such as a concentration, stage or amount of the condition.

From the input values and the output value, the present method is capable of estimating or the identification of mathematical correlations between the input values and the output value.

In a first aspect, the invention relates to a method of deriving a correlation between observed values, the method comprising:
a) observing a plurality of data sets each comprising a plurality of first values and at least a second value from a process, the process generating a resulting product, the first values being observed during the process and the second value(s) from the resulting product,
b) generating a data flow structure representing:
a detecting node,
a plurality of nodes, each node capable of:
select a mathematical function from a predetermined group of functions and
select another node or the detecting node,
c) for each of a plurality of runs:
selecting one input node, of the plurality of nodes, for each first value,
sequentially, selecting a mathematical function and a next node or the detecting node, until no more nodes are selected,
logging the input nodes and which first value they relate to as well as, for each input node and each selected node:
which mathematical function was selected, and
which node or the detecting node was selected, and
combining the mathematical functions, on the basis of the logged nodes, the order thereof and the mathematical functions thereof, into one or more final mathematical functions, and
d) deriving the correlation by:
for each data set and each final mathematical function:
determining an output value of the final mathematical function by entering the first values of the data set into the mathematical function, and
comparing the output value to the second value of the data set,
selecting, from the comparisons, the final mathematical function generating the output values corresponding best to the pertaining second values.

In this context, the steps of the method need not be in the described order.

The process and the observed values may be any type of process and any type of values. A process may be a process of manufacturing an element or creating an element. The process may be a chemical process, where the first values may relate to initial or intermediate ingredients or additives and where the second value may relate to a desired parameter of the resulting product. The resulting product need not be the final product of the process. The resulting product in this context may be an intermediate product of an overall process.

A data set is a set of values where the second value(s) is/are determined from the process based on or resulting from the first values or the ingredients/additives/parameters from which the first values are determined.

Multiple data sets are determined, such as over time, where at least one value varies between data sets. Data sets may be determined over time, such as by varying parameters of the process or by repeating the process with different parameters, where the parameters are represented in at least some of the first values.

Having then arrived at the correlation between the first and second values, a better control of the process may be achieved to optimize a property quantified or indicated by the second value.

The process may be a chemical process where initial ingredients/parameters may be varied in some sense, such as concentrations, temperature, time and the like.

Some processes are not easily seen through, such as processes in the human body. Thus, the potency of a drug or the risk of contracting a disease may be desired predictable even though the actual process may be a black box. In that situation, the first values may be parameters of a drug delivered to a person, such as dose size, number of doses, times between doses, or characteristics of the person, such as age, sex, blood pressure, whether the person has a particular gene defect or not, whether a person has a certain condition or not, or a quantification such as temperature, immune response, oxygen uptake, number of T cells per ml blood, and the like. The second value may relate to whether the person contracts the disease or not, or an immune response of the person, or the like.

In general, the first values need not be known to be influential in the result and thus the second value. The present method can be used to rule out irrelevant or less important values. This may be a part of the result of the method.

The values are observed in any desired manner. This observation may be a sensing/detection or the like of the values. A value may be a real number, such as a concentration or weight, a binary number, such as whether a gene defect is present or not, or the like.

The data flow structure may be implemented in a plurality of manners. Specific hardware may be built creating this structure or a software programmed architecture may be programmed to embody the data flow structure.

The structure comprises a detecting node. In fact, multiple detecting nodes may be employed. The detecting node marks the end of a sequence of selected nodes. If multiple detecting nodes are employed, different detecting nodes may form the end of different paths or different sequences of selected nodes so that more candidates are available for the analysis described below.

A plurality of nodes is provided which are capable of selecting one or more other nodes as well as a mathematical function.

Any number of nodes may be provided. All nodes may be able to select all nodes. Alternatively, a node may be allowed to only select some nodes. In a preferred embodiment, the nodes are, at least virtually, provided at intersections in a grid and allowed to only select the nearest neighbours. For each node, a set of other nodes may be defined which may be selected.

A number of runs are performed. Each run comprises selecting one input node for each first value. Multiple input nodes may be selected for any input value. In each input node, a mathematical function will be selected as well as another node or the detecting node.

Then, the data flow structure performs its operation: each selected node selects a mathematical function as well as another node or the detecting node. This process may continue until no more nodes are being selected. This state or situation may be ascertained or determined in a number of manners. In one manner, account is made of each node newly selected. The node may be deleted from this group/list once it has selected another node, which is then put on the list or added to the group. The list becomes shorter, when a node selects the detecting node, which is not put on the list. Alternatively, a search may be made through the structure for nodes which have been selected and which have not yet selected another node.

In a preferred embodiment, tokens may be simulated flowing through the flow structure from each input node to the selected nodes and so on, until all tokens are received by the detecting node. When all tokens are at the detecting node, the process has stopped. For each token, the order of the nodes and their individually selected mathematical functions may now be combined into a final mathematical function.

No more nodes are selected when, for example, no nodes, apart from the detecting node, exist which have been selected and which have themselves not selected another node or the detecting node.

The input nodes, the selected nodes as well as the mathematical functions selected are logged. Then, final mathematical functions are determined by combining the mathematical functions selected in each node of a sequence of nodes, selecting each other, as well as the order thereof.

A run starts with the selection of a plurality of input nodes initiating the sequences of selections until the detecting node is selected. Each sequence of selected nodes may be denoted a path and each run thus may comprise a plurality of paths. Each selected input node may represent in a path. Below, path merging is described, so that a run may comprise fewer paths than the number of selected input nodes.

It is noted that each node may select the mathematical function from a predetermined group of mathematical functions. This selection may be random or may be based on a weight distribution between the available mathematical functions so that one mathematical function may be more likely to be selected than others.

Also, each selected node may select the next node on a random basis. Alternatively, a weight distribution may be used between the other nodes or the nodes to which this node is allowed to select, including the detecting node, so that one node is more likely to be selected than others.

For each selecting of the detector node, the sequence of selected nodes from the initial node(s) and to the detecting node is determined or logged. Also, the mathematical function(s) are logged. This sequence will define the final mathematical function of that path. The order of the mathematical functions will have an impact on the final mathematical function. Clearly, a squaring function and a sine function will, when combined, give different outputs depending on whether the squaring function is performed initially or last. The order of the mathematical functions, when determining the final mathematical function, may be any predetermined order. In principle, any order may be selected as long as it is reproducible, but it may be preferred that the order of the selection of the mathematical functions (or the reverse order thereof) is used, as this is the simplest method.

The final mathematical functions are then candidates for the correlation sought for.

Having then determined the final mathematical functions, each final mathematical function is performed on the initial values of each data set to generate a plurality of output values. For each final mathematical function and data set, the resulting output value is then compared to the second value of the data set.

Now, from these comparisons, the final mathematical function may be selected, the output value of which corresponds the best to the pertaining second value. In this respect, the comparison may be a simple comparison between numbers and that or those output data which is/are the closest may be identified.

A final mathematical function is checked for each data set, so a mathematical function may be evaluated across data sets by e.g. deriving, for each final mathematical function, a value derived from the comparisons of all output values and the second values of the data sets. This final value could be e.g. based on a sum, over all data sets, of squared differences between the output value and the second value of each data set. A large number of manners exist of selecting one method over a plurality of methods across a number of data sets.

Naturally, some parameters of a process may interact, so that it would be desirable to facilitate this by allowing a node to be configured to, if selected by two nodes, select a mathematical function from a group of functions accepting two variables.

Having been selected by two nodes, the node may be configured to still select only one next node. Then, the first values interact in the sense that the output data will depend on both input values as well as the function selected.

Then, the nodes may have two groups of mathematical functions available, one for the situations when the node is selected by only a single node and another for the situations where the node is selected by two nodes.

Clearly, nodes may be capable of selected by more than two nodes. In that situation, functions should be available able to handle the required number of input data.

Also, it may be desired to allow a node to select more than a single, next node. In that situation, multiple paths, having common portions/nodes, will be formed.

It may be desired that all nodes select the next node synchronously. In this context, "synchronously" need not be at exactly the same point in time, but it may be desired that all nodes perform the selection or are selected at at least substantially the same time. For example, all nodes may be selected within a period of time before that point in time. Then, delays and the like may be taken account, as is seen in both hardware centric set-ups and software controlled set-ups, usually based on heavily parallel architectures. This is especially relevant when a node needs to determine whether it has been selected by one or two (or more) nodes. These selection decisions need not be made at exactly the same point in time, but in this manner, the node may select the correct type of mathematical function at a point in time where it has been ascertained that all nodes have made their selections. Then, delays will not result in a situation where a node makes the wrong decision/selection before being selected by all relevant nodes.

Thus, a clocking signal may be provided, or the method may ensure that all nodes make their selections of the next node(s), before the mathematical functions are selected and the next node(s) is/are selected.

Then, the runs/paths may be determined to be at an end, when a point in time occurs where no nodes are to select mathematical function and next node(s). This will be when all paths/runs have ended in the detecting node(s), which is not capable of selecting further nodes.

The present method has a number of applications, in one situation, the observing step comprises at each time:
  providing a number of ingredients for the process and
    determining a first value from each of a plurality of the ingredients and
  deriving the second value from a resulting product of the process and
the method further comprising the subsequent steps of:
  determining from the correlation alternative ingredients and
  carrying out the process with the alternative ingredients.

In this situation, the correlation describes how the ingredients, characterized by the first values, influence the parameter of the resulting product. Thus, this correlation may be used for selecting optimal, such as alternative ingredients, where an alternative may be the same ingredient in another concentration or amount.

The alternative ingredients, for example, may be determined by reverse calculation from a desired second value, which characterizes an optimal or desired final product, to arrive at first values which, by the correlation, result in the desired second value. As the correlation is a simulation or representation of the process, using ingredients represented by the first values, is expected to provide a final product represented by the desired second value.

Naturally, one or more of the first values may relate not to ingredients but to process parameters, such as timing between adding ingredients, temperatures or the like. Then, also this parameter may be derived from the reverse calculation.

In other situations, the correlation relates to drugs administered to a human and/or animal body, where, based on the correlation, the next step could be to determine, from the correlation, an altered amount, concentration, size of one or more doses and/or altered periods of time between doses and/or other drugs or combinations thereof and administering the altered dose(s) to one or more humans or animals.

As described above, the step of selecting the mathematical function may comprise selecting the mathematical function based on a first distribution function representing, for each of the functions in the predetermined group of functions, a probability of the pertaining function being selected. Then, from the selected final mathematical function, the pertaining nodes selected and the mathematical functions selected by the nodes are identified and, in the input node(s) and each identified node, increasing the probability of selecting the pertaining selected mathematical function. Repeating steps c) and d) now results in a new set of final mathematical functions which are biased toward the selected final mathematical function of the first or former iteration of steps c) and d). This biasing will tend to arrive at final mathematical functions with similarities with the former selected final mathematical function but may perform better.

In addition or alternatively, the step of selecting the node may comprise selecting the node based on a second distribution function representing, for each of the nodes, a probability of the pertaining node being selected. Then, from the selected final mathematical function, the pertaining nodes selected by the nodes are identified and, in the input node(s) and each identified node, increasing the probability of selecting the pertaining selected node. Repeating steps c) and d) now results in a new set of final mathematical functions which are biased toward the selected final mathematical function of the first or former iteration of steps c) and d). This biasing will tend to arrive at final mathematical functions with similarities with the former selected final mathematical function but may perform better.

Clearly, the above may be re-iterated so as to further adapt the first distribution functions.

Figure 2:
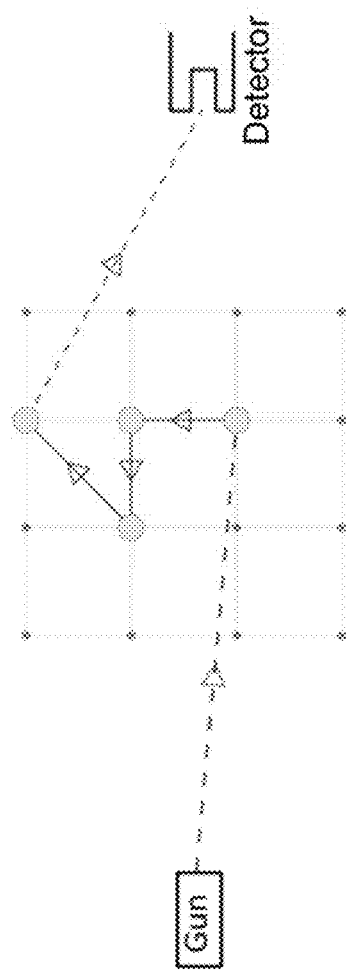
Figure 3:
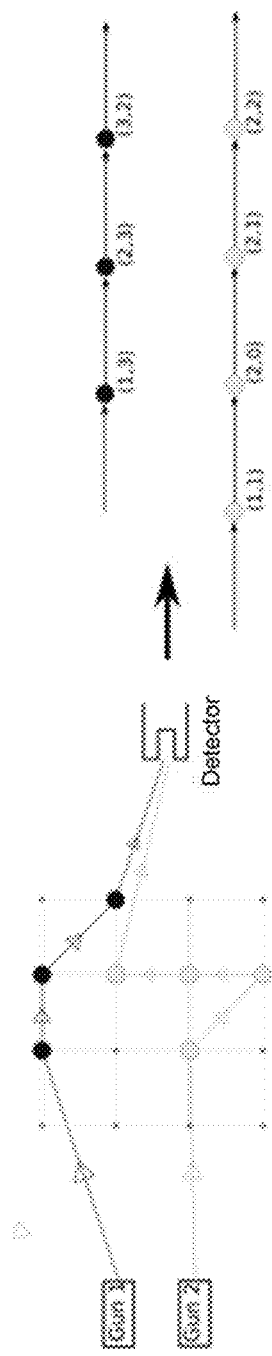
Figure 4:
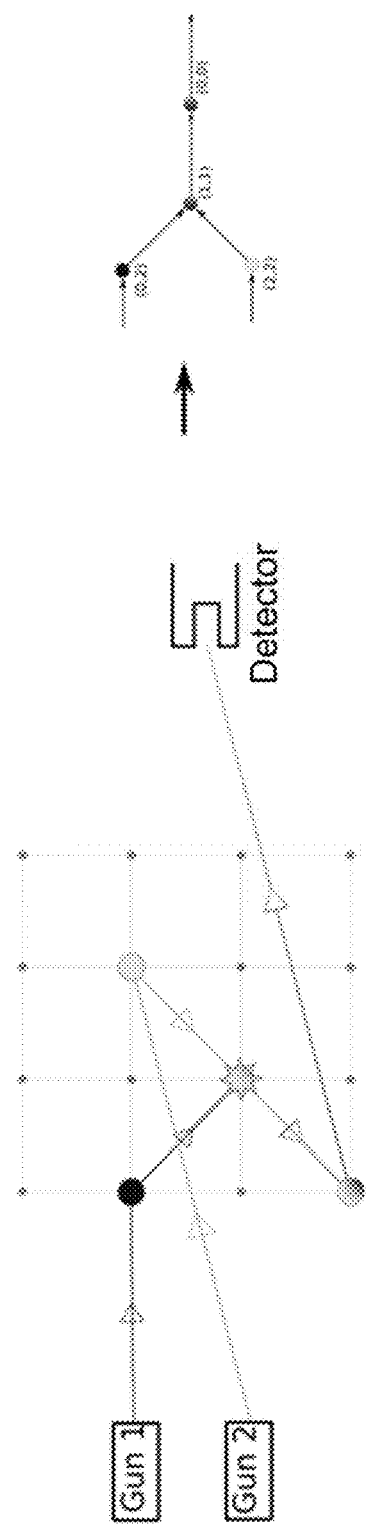
Figure 5:
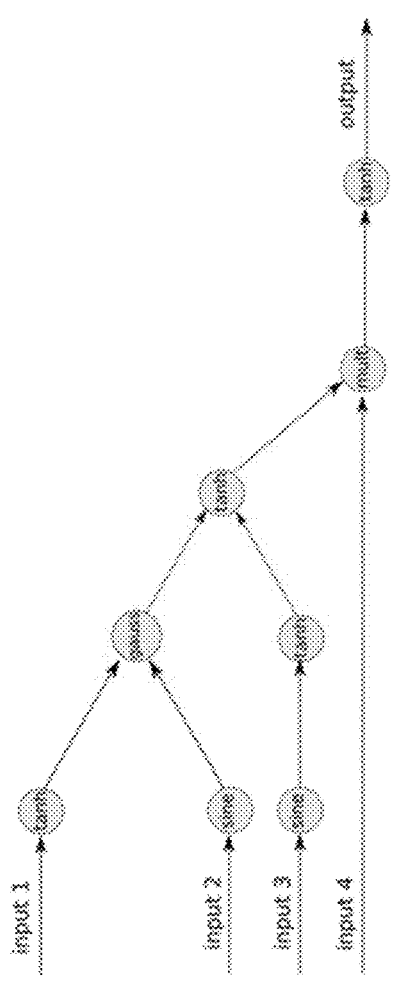
Figure 6:
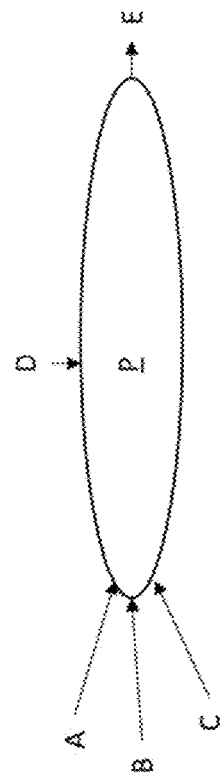

In the following, preferred embodiments of the invention will be described with reference to the drawing, wherein:

FIG. 1 illustrates a 2-dimensional structure of nodes, a gun distribution and a node distribution, FIG. 2 illustrates a path in the structure of FIG. 1, FIG. 3 illustrates two paths, FIG. 4 illustrates combination of information in nodes and corresponding function graphs, FIG. 5 illustrates a function graph, and FIG. 6 illustrates a process.

In FIG. 1, a data structure illustrating a two-dimensional lattice 10 is illustrated having a plurality of nodes 12. In this structure, a node may communicate with any of the neighbouring nodes in the structure. Communication in the lattice is by transmission of particles or tokens from node to node. In this structure, as illustrated, each node has 8 neighbouring nodes from which it may receive tokens and to which it may output tokens.

A gun 14 is illustrated which is capable of launching tokens to the nodes.

A detector 16 is illustrated which may receive tokens from the nodes 12.

The manner in which the structure operates is that the gun launches a token into a node which transmits the token to one of the nodes with which it is able to communicate, and that this function goes on until a node launches the token to the detector.

The selection, in the gun, of which initial node to forward the token to is determined by a distribution function of the gun. From this, an initial node is selected. Also, each node comprises a distribution function describing the relative weights or probabilities for each of the other nodes to which this node can forward tokens. Thus, the determination of to which next node to feed the token to is made based on this distribution function. The distribution function for the node will also include the detector, allowing a mechanism for feeding tokens to the detector and thus ending the path.

As will be described below, a node will select a mathematical function when receiving a token. Thus, as the token moves through the nodes, each node will select a mathematical function, so that the functions selected and the order thereof determined by the order in which the nodes received the token will determine a final mathematical function (see below).

A path, in this context, will be the sequence of nodes visited by a token from the gun to the detector. A path is seen in FIG. 2. A path thus results in a final mathematical function.

The same could be obtained if initial information was fed into the first node which performed the selected function on the input information to arrive at altered information which was transmitted to the next node which would perform its selected mathematical function on the received information to again arrive at amended information. This would be repeated until the detector was selected which would then receive the output value of the last node. This output value will be the resulting function performed on the initial information.

In each node, a multiple of mathematical functions is available. Thus, when a node receives a token it will select a mathematical function usually among a plurality of available or predetermined mathematical functions. The function is selected based on a distribution function in the same manner as the next node is selected.

Relevant functions could be multiple, such as $x^2$, $x^3$, $sin(x)$, $x^2+y^2$, $tan\ h(Wx+y)$, $gauss(x)$, $sin(Wx+y)$, where W and y may be randomly selected or randomly chosen for the complete operation.

Clearly, launching, sequentially, tokens from the gun will arrive at different paths and thus different final mathematical equations.

Thus, the token's path through the grid and the mathematical functions selected is based on distribution functions which, as will be described below, may be altered or optimized.

As seen in FIG. 3, multiple tokens may be launched into the structure at the same time from the same or different guns. In this situation, tokens will move in the grid at the same time. This may result in different paths as is seen in FIG. 3, where each token moves from gun to detector along its own path. However, as seen in FIG. 4, situations may then occur where two tokens arrive at the same node. Clearly, the node could simply select a mathematical function for each token and a next node for each token, so that the tokens again had individual paths. However, in this situation, the node preferably selects a mathematical function which is able to receive two variables and then output a single token.

Mathematical functions suitable for receiving two variables may be subtraction, multiplication, division, but also $tan\ h(W_1x+W_2y+b)$, $gauss(x,y)$, or the like, where x and y are the two variables and $W_1$, $W_2$ and b are randomly selected, such as for the complete operation.

Naturally, functions may be available capable of receiving even more variables.

This again results in a final mathematical equation which now has more than one variable.

To be able to determine that two tokens arrive at the same node at the same time, it may be desired to transport tokens from node to node in a coordinated fashion, such as simultaneously in the grid. Thus, all tokens are transported at the same time. For this purpose, a general clock is provided which controls the token flow. For each beating of shifting of the clock, the tokens are exchanged between transmitting and receiving nodes. Then, when a node receives two tokens at the same time, a suitable function is selected.

Thus, in such instances, launching one number of tokens into the grid will result in a fewer number of tokens received by the detector.

Again, a sequence of launches, where each launch feeds multiple tokens into the grid at the same time, will arrive at a number of final mathematical functions, some of which may have multiple variables.

To put the grid and the functions into a practical perspective, consider a process, such as a chemical process where a number of observations are made from initial parameters such as ingredients or process parameters and where a resulting or second value is determined from an intermediate product or an end product of the process. Then, it would be desirable to learn how the second value depends from the initial value to e.g. optimize the end product by arriving at a predetermined value for the second value—by adapting the initial parameters.

In FIG. 6, a process P is seen in which a number of ingredients A, B and C are processed under conditions or parameters D to an end result E. The ingredients A, B and C may be characterized by values, which may be the first values. The process parameter D may also be a first value, and the end result or product E may be characterized by a value which may be a second value.

Thus, the process converts the ingredients using the parameter D into the end result.

This conversion may be simulated or equated to a mathematical conversion of the values A, B and C (and potentially D) into E. Having determined this mathematical conversion, it may be possible to determine an optimal or desired end product or value E and estimate relevant values A, B, C and/or D which the process will convert into the desired end product.

Thus, a mathematical function is desired into which the initial parameters, or at least some of these, are entered where the output of the function corresponds or correlates to the parameter of the end/intermediate product.

Thus, firing into the grid a number of tokens corresponding at least to the number of initial parameters and assigning an initial parameter to each token will arrive at a number of final mathematical functions from which output values may be generated when entering the pertaining initial values. These output values may then be compared to the second value from the process.

This process may be repeated, so that the guns are fired sequentially a number of times and the resulting mathematical functions identified. Each firing of the guns may be called a "run". As mentioned, the paths of the tokens and the mathematical functions selected in the nodes are selected from distribution functions so that each run (firing of the guns) will probably arrive at a different a different final mathematical function or a selection of different final mathematical functions.

From a number of runs, a number of different final mathematical functions will be arrived at which will include different variables (initial values). All final mathematical functions may then be tested by feeding the pertaining initial parameters into the functions and comparing the output information to the pertaining second value.

Clearly, multiple sets of initial values and second value may be obtained from the process so that each set is used with the functions from each run.

From the comparison of each final mathematical function across all sets of values, an overall performance or correlation of the final mathematical function may be arrived at. This determination may be made in a number of manners, such as a square root of the differences, squared, between the output value and the second value of each set. In other situations, a correspondence between the output value and input parameters may be sought for, so that final mathematical functions comprising this correspondence are favoured. For example, it may be expected that two initial values have an effect on each other so that a mathematical function comprising both would be expected. One or more initial values may be known to have an effect on the second value and thus may be required in the final mathematical function.

Also, a final mathematical function may be selected with a particular number, a minimum number or a maximum number of variables or mathematical operations therein. In this manner, the complexity or simplicity of the final function may be affected. Compared to standard AI methods from which the correlation is obscure, this makes it possible to select a correlation which is simple.

Having now identified the optimal or desired final mathematical function, the run or path may be accessed, and the nodes and mathematical functions identified.

Then, the distribution functions of the gun(s), and the nodes of the run/paths may be altered so as to favour the run/paths taken by the tokens to arrive at the final mathematical function. Thus, in each of the nodes, the distribution function for selecting the mathematical function may be altered so that the probability of selecting that mathematical function is increased compared to the other selectable mathematical functions. Also, in the node, the distribution function for selecting the next node or the detector is altered to increase the probability of the next node or the detector of this particular path/run to be selected compared to the other nodes/detector.

Then, firing again the guns to feed tokens into the modified grid, portions of the former, optimal final mathematical function are given higher probabilities. Thus, tokens may travel outside of the nodes of the path/run leading to that function but may find themselves in a node thereof and thus follow that path/run to the detector or for a bit and then move outside of the path/run again. Thus, modifications or mutations are seen of the (original) final mathematical function of the first runs.

Again, a number of runs may be performed in each of which the guns fire tokens and the detector collects tokens and wherein final mathematical functions are derived. These final mathematical functions now will have similarities with the "original" final mathematical function and thus may well provide an even better correlation between the values of the data sets.

This operation of adapting the grid and performing new runs may be repeated any number of times.

In principle, a node may also be able to receive single token, select a mathematical function and then output two tokens to each of two other nodes. This would merely correspond to the process of FIG. 2 where two paths have common initial portions.

Clearly, the 2-dimensional structure of FIG. 1 may be extended into any dimension, such as 3-dimensional. Then, the nodes will be able to output tokens to nodes of other dimensions. More dimensions allow more different paths to be found even though some nodes are, due to their weight functions, more biased toward a particular path. Thus, the more dimensions, the more optimizations or updates may be made and the better a simulation may be arrived at.

The invention claimed is:

1. A non-transitory computer-readable storage medium storing program code that is executable by a computing device to cause the computing device to
implement a data flow structure, the data flow structure comprising:
a two-dimensional lattice of a plurality of nodes;
a gun that is configured to
select one node of the plurality of nodes as an input node according to a distribution function associated with the gun, and
transmit a token to the input node; and
a detecting node configured to receive tokens from the plurality of nodes,
wherein each node of the plurality of nodes is configured to, in response to receiving one token from the gun or a neighboring node of the plurality of nodes,
select a mathematical function from a predetermined group of functions such that the selected mathematical function is added to a sequence of mathematical functions defining a final mathematical function, or
select a next node to which to forward the one token, where the next node is the detecting node or another neighboring node of the plurality of nodes, and
transmit the one token to the selected next node, and
determine a final mathematical function based on
causing the gun to transmit the token to the input node,
tracking a sequence of nodes of the plurality of nodes traversed by the token from the gun to the detecting node, and
in response to the token being received at the detecting node from the gun via the sequence of nodes, logging a sequence of mathematical functions that are each selected by a separate node of the sequence of nodes, in an order corresponding to an order of the separate nodes of the sequence of nodes, to define the final mathematical function.

2. The non-transitory computer-readable storage medium of claim 1, wherein the program code is executable by the computing device to cause the computing device to:
observe a plurality of data sets each comprising a plurality of first values and at least a second value from a production process, the production process manufacturing a resulting product from a plurality of ingredients, one of the plurality of first values being determined from each ingredient of the plurality of ingredients, the second value being derived from at least one resulting product of the production process,
execute a plurality of runs of the data flow structure such that each run of the plurality of runs includes
causing the gun to select one particular node, of the plurality of nodes, as the input node for each first value,
causing the gun to transmit the token to the input node,
tracking the sequence of nodes traversed by the token, where each node of the sequence of nodes selects a particular mathematical function in response to receiving the token,
logging each selected input node of the plurality of nodes and which first value the selected input node relates to as well as, for each input node and each node of the sequence of nodes traversed by the token from the selected input node to the detecting node, which mathematical function was selected by the each node, and
which node or the detecting node was selected by the each node, and
combining mathematical functions selected by the sequence of nodes, on the basis of the logged input nodes, the order of the sequence of nodes from each input node and to the detecting node, into one or more final mathematical functions,
deriving a correlation by for each data set of the plurality of data sets and each final mathematical function of the one or more final mathematical functions, determining an output value of the final mathematical function by entering the first values of the data set into the final mathematical function, and comparing the output value to the second value of the data set, and selecting, from the comparisons, a particular final mathematical function, of the one or more final mathematical functions, that is determined to generate output values corresponding best to the pertaining second value, among the output values generated by the one or more final mathematical function, and determining, from the correlation, alternative ingredients, and carrying out the production process to manufacture the resulting product with the alternative ingredients.

3. A computing device, comprising:

a memory storing program code; and a processor configured to execute the program code to implement a data flow structure, the data flow structure comprising:

a two-dimensional lattice of a plurality of nodes;

a gun that is configured to select one node of the plurality of nodes as an input node according to a distribution function associated with the gun, and transmit a token to the input node; and a detecting node configured to receive tokens from the plurality of nodes, wherein each node of the plurality of nodes is configured to, in response to receiving one token from the gun or a neighboring node of the plurality of nodes, select a mathematical function from a predetermined group of functions such that the selected mathematical function is added to a sequence of mathematical functions defining a final mathematical function, or select a next node to which to forward the one token, where the next node is the detecting node or another neighboring node of the plurality of nodes, and transmit the one token to the selected next node, and determine a final mathematical function based on causing the gun to transmit the token to the input node, tracking a sequence of nodes of the plurality of nodes traversed by the token from the gun to the detecting node, and in response to the token being received at the detecting node from the gun via the sequence of nodes, logging a sequence of mathematical functions that are each selected by a separate node of the sequence of nodes, in an order corresponding to an order of the separate nodes of the sequence of nodes, to define the final mathematical function.

4. The computing device of claim 3, wherein the processor is configured to execute the program of instructions to:

observe a plurality of data sets each comprising a plurality of first values and at least a second value from a production process, the production process manufacturing a resulting product from a plurality of ingredients, one of the plurality of first values being determined from each ingredient of the plurality of ingredients, the second value being derived from the resulting product of the production process, execute a plurality of runs of the data flow structure such that each run of the plurality of runs includes causing the gun to select one particular node, of the plurality of nodes, as the input node for each first value, causing the gun to transmit the token to the input node, tracking the sequence of nodes traversed by the token, where each node of the sequence of nodes selects a particular mathematical function in response to receiving the token, logging each selected input node of the plurality of nodes and which first value the selected input node relates to as well as, for each input node and each node of the sequence of nodes traversed by the token from the selected input node to the detecting node, which mathematical function was selected by the each node, and which node or the detecting node was selected by the each node, and combining mathematical functions selected by the sequence of nodes, on the basis of the logged input nodes, the order of the sequence of nodes from each input node and to the detecting node, into one or more final mathematical functions, derive a correlation by for each data set of the plurality of data sets and each final mathematical function of the one or more final mathematical functions, determining an output value of the final mathematical function by entering the first values of the data set into the final mathematical function, and comparing the output value to the second value of the data set, and selecting, from the comparisons, a particular final mathematical function, of the one or more final mathematical functions, that is determined to generate output values corresponding best to the pertaining second value, among the output values generated by the one or more final mathematical function, and determine, from the correlation, alternative ingredients, and carry out the production process to manufacture the resulting product with the alternative ingredients.

* * * * *